(12) United States Patent
Koo

(10) Patent No.: US 8,097,421 B2
(45) Date of Patent: Jan. 17, 2012

(54) METHOD FOR PERFORMING A MULTIPLEX IMMUNOASSAY USING LABEL DISASSOCIATION AND AN INTEGRATED SUBSTRATE

(75) Inventor: Tae-Woong Koo, Cupertino, CA (US)

(73) Assignee: Intel Corporation, Santa Clara, CA (US)

( * ) Notice: Subject to any disclaimer, the term of this patent is extended or adjusted under 35 U.S.C. 154(b) by 309 days.

(21) Appl. No.: 11/319,791

(22) Filed: Dec. 29, 2005

(65) Prior Publication Data

US 2007/0154881 A1  Jul. 5, 2007

(51) Int. Cl.
| | |
|---|---|
| C12M 1/34 | (2006.01) |
| C12M 3/00 | (2006.01) |
| C12N 11/00 | (2006.01) |
| C12N 11/16 | (2006.01) |
| G01N 21/00 | (2006.01) |
| G01N 33/00 | (2006.01) |
| G01N 33/48 | (2006.01) |
| G01N 15/02 | (2006.01) |
| B01L 3/00 | (2006.01) |
| C07K 17/00 | (2006.01) |

(52) U.S. Cl. ... 435/7.1; 435/287.2; 435/174; 435/288.5; 435/287.3; 435/288.7; 422/82.05; 422/68.1; 422/502; 506/4; 530/350; 356/335

(58) Field of Classification Search .......... None
See application file for complete search history.

(56) References Cited

U.S. PATENT DOCUMENTS

| | | | | |
|---|---|---|---|---|
| 6,506,609 B1 * | 1/2003 | Wada et al. | .......... | 436/148 |
| 6,635,469 B1 * | 10/2003 | Litt et al. | .......... | 435/287.1 |
| 6,743,581 B1 * | 6/2004 | Vo-Dinh | .......... | 435/6 |
| 2003/0207290 A1 * | 11/2003 | Kenten et al. | .......... | 435/6 |
| 2004/0086424 A1 * | 5/2004 | Schembri | .......... | 422/58 |
| 2005/0191687 A1 * | 9/2005 | Wang et al. | .......... | 435/6 |
| 2005/0250117 A1 * | 11/2005 | Su et al. | .......... | 435/6 |
| 2006/0078998 A1 * | 4/2006 | Puskas et al. | .......... | 436/64 |
| 2006/0205061 A1 * | 9/2006 | Roukes | .......... | 435/287.2 |
| 2006/0211055 A1 * | 9/2006 | Hafeman et al. | .......... | 435/7.5 |

OTHER PUBLICATIONS

Sato et al (Electrophoresis 23:743-739, 2002).*
Choi et al (Biomedical Microdevices 3:191-200, 2001) i.*
Wang et al (Biosensors and Bioelectronics 21:419-425, 2005).*
Tsitsilonis et al "Serological detection of hepatitis B virla infection by a panel of solid-phase enzyme-linked immunosorbent assays (ELISA)" Journal of Pharmaceutical and Biomedical Analysis, 2004, 34: 811-822.*
Vo-Dinh et al, "DNA biochip using a phototransistor integrated circuit," published in Analytical Chemistry, 1999, vol. 71, No. 2, pp. 358-363.
Topol et al, Enabling technologies for wafer-level bonding of 3D MEMS and integrated circuit structures, published in Electronic Components and Technology Conference, 2004. Proceedings. 54th, published Jun. 1-4, 2004, vol. 1, pp. 931-938.

* cited by examiner

*Primary Examiner* — Betty Forman
*Assistant Examiner* — Joseph G Dauner
(74) *Attorney, Agent, or Firm* — Pillsbury Winthrop Shaw Pittman LLP

(57) ABSTRACT

The application relates to a method, system and device for performing biological assays. The method, system and device allow more accurate and specific detections of biomolecules in multiplex assays, such as immunoassays and DNA microarray assays. More specifically, the embodiments of the invention allow the detection of labels after their detachment or disassociation from a binding situation wherein interference from other labels or the background may reduce the accuracy of specificity of the detection. The embodiments of the invention further allow detection of individual labels.

34 Claims, 6 Drawing Sheets

Disassociation of Labels or Label-Conjugated Molecules
from the Surface of the Substrate in an Immunoassay

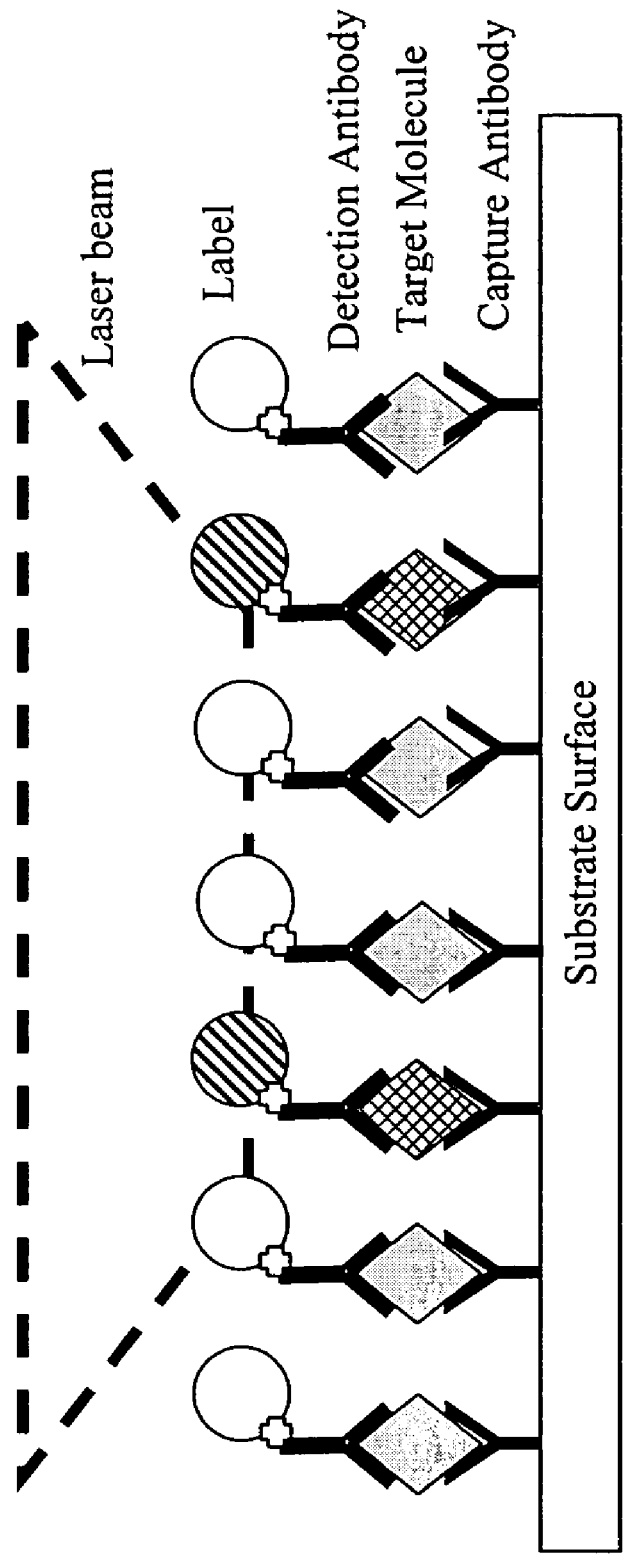
FIG. 1   Conventional Sandwich Immunoassay

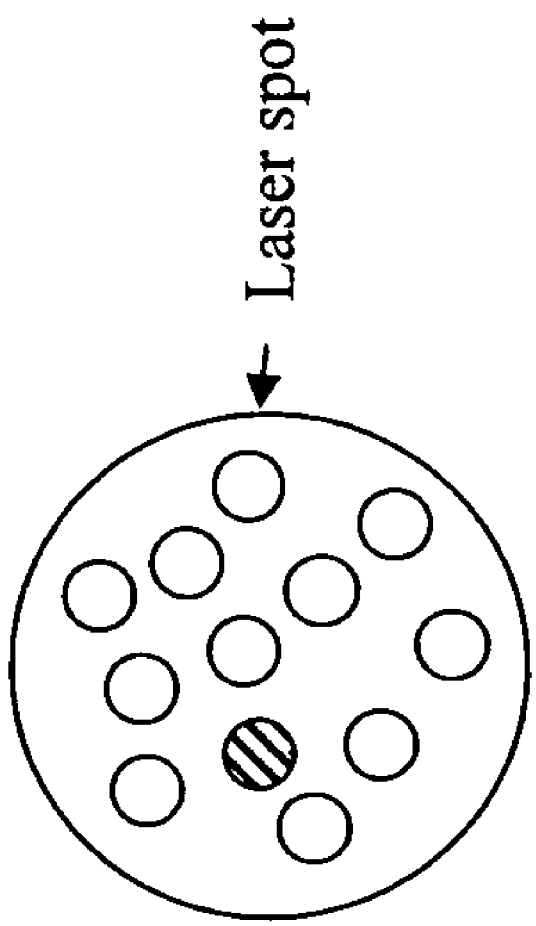
FIG. 2  Detection in Conventional Immunoassay

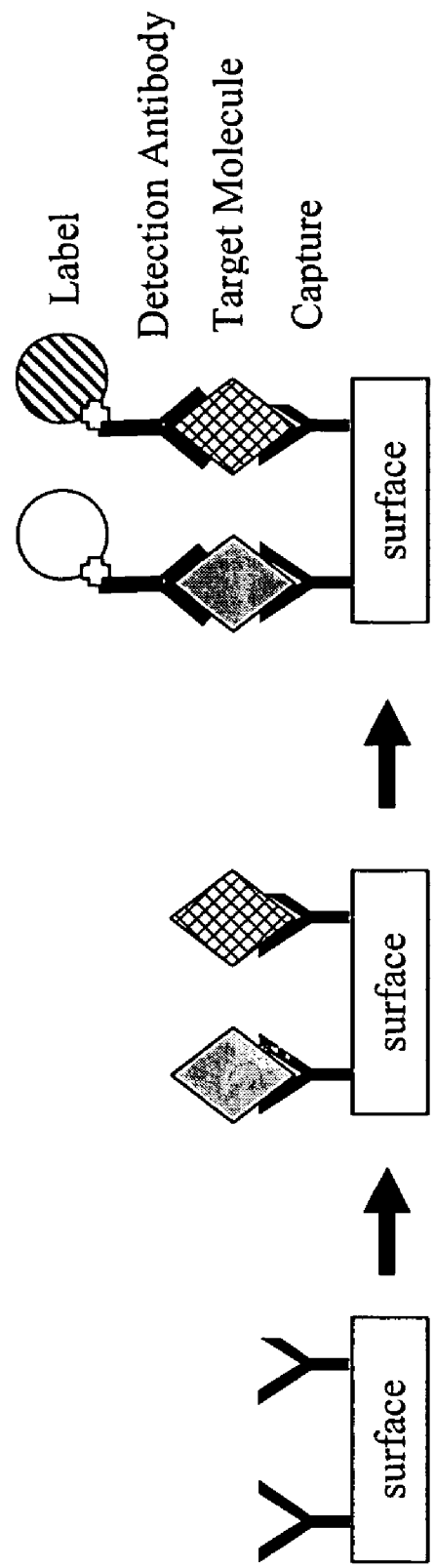
FIG. 3   Steps in Conventional Sandwich Immunoassay

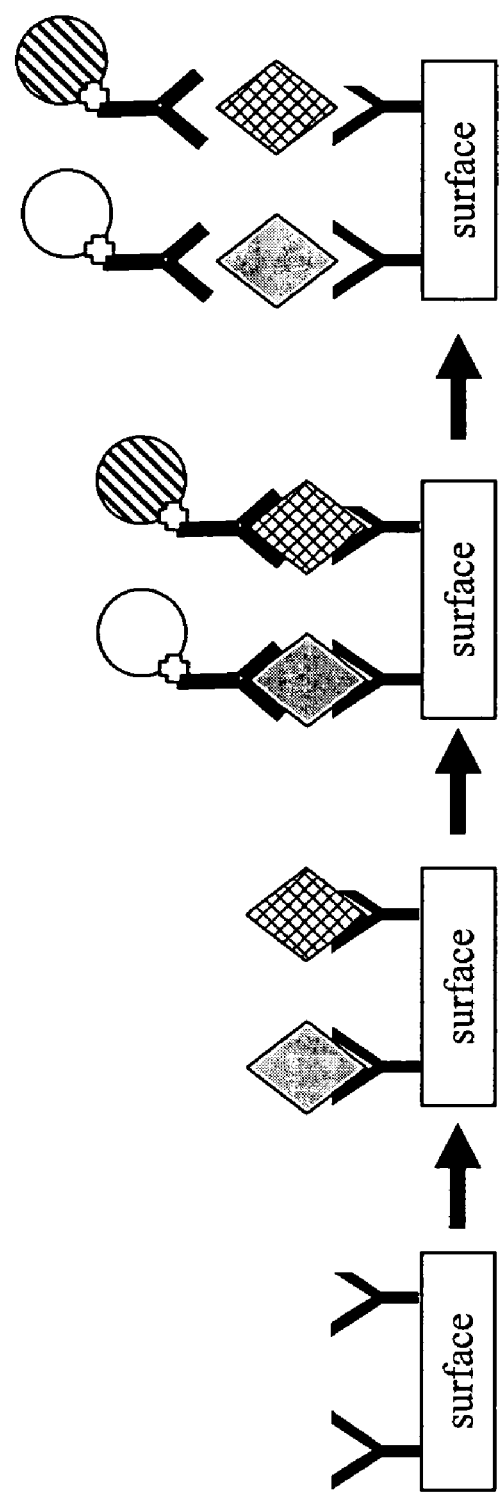
FIG. 4  Disassociation of Labels or Label-Conjugated Molecules from the Surface of the Substrate in an Immunoassay

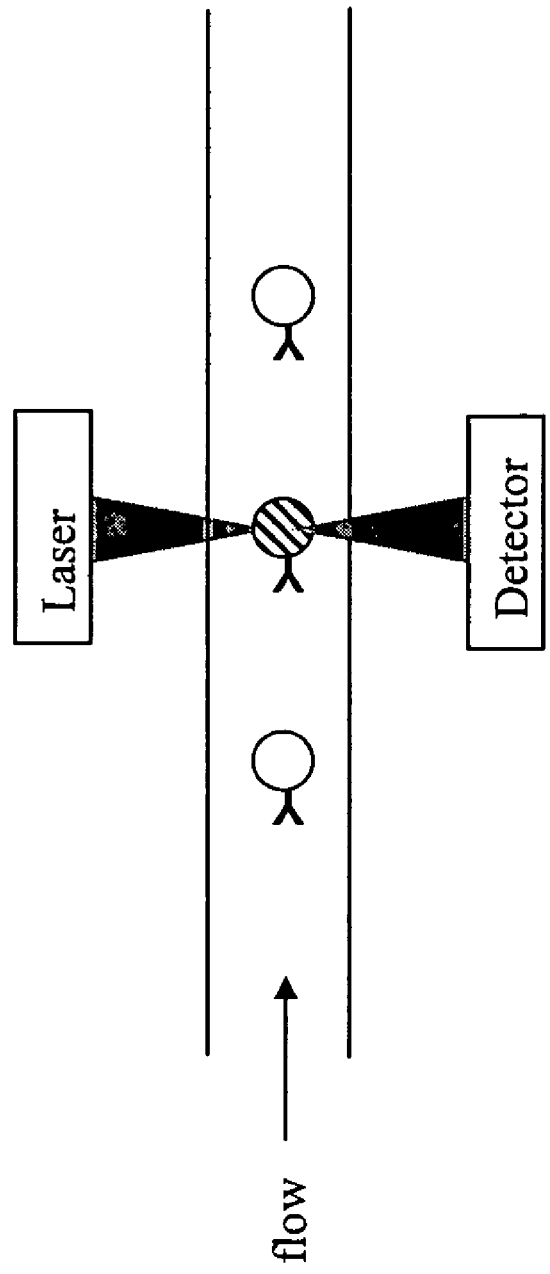
FIG. 5  Detection of Individual Labels in an Analyzer

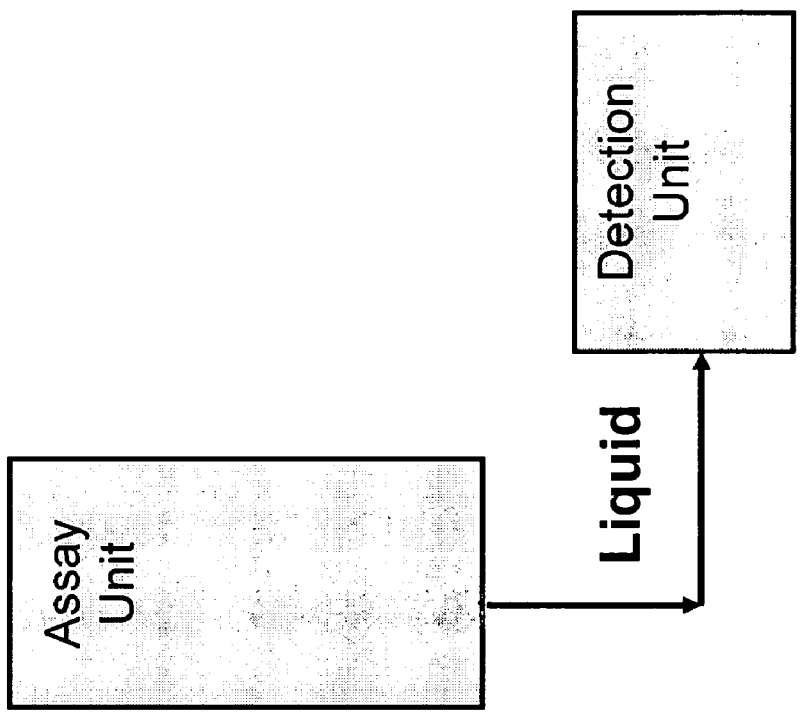
FIG. 6  A System Containing an Assay Unit and a Detection Unit

METHOD FOR PERFORMING A MULTIPLEX IMMUNOASSAY USING LABEL DISASSOCIATION AND AN INTEGRATED SUBSTRATE

RELATED APPLICATIONS

None

FIELD OF INVENTION

The embodiments of the invention relate to a method, system and device for performing biological assays, especially multiplex biological assays, and to the detection of particles, biomolecules and cells, especially on an individual molecule or particle basis. The invention transcends several scientific disciplines such as, biochemistry, physics, immunology, molecular biology, and medical diagnostics.

BACKGROUND

Rapid and specific detections of biological cells and biomolecules, such as red blood cells, white blood cells, platelets, proteins, DNAs, and RNAs, have become more and more important to biological assays crucial to fields such as genomics, proteomics, diagnoses, and pathological studies. For example, the rapid and accurate detection of specific antigens and viruses is critical for combating pandemic diseases such as AIDS, flu, and other infectious diseases. Also, due to faster and more specific methods of separating and detecting cells and biomolecules, the molecular-level origins of disease are being elucidated at a rapid pace, potentially ushering in a new era of personalized medicine in which a specific course of therapy is developed for each patient. To fully exploit this expanding knowledge of disease phenotype, new methods for detecting multiple biomolecules (e.g., viruses, DNAs and proteins) simultaneously are required. The multiplex biomolecule detection methods must be rapid, sensitive, highly parallel, and ideally capable of diagnosing cellular phenotype in vivo.

A specific type of biological assay increasingly used for medical diagnostics, as well as in food and environmental analysis, is immunoassay. An immunoassay is a biochemical test that measures the level of a substance in a biological liquid, such as serum or urine, using the reaction of an antibody its antigen. The assay takes advantage of the specific binding of an antibody to its antigen. Monoclonal antibodies are often used as they only usually bind to one site of a particular molecule, and therefore provide a more specific and accurate test, which is less easily confused by the presence of other molecules. The antibodies picked must have a high affinity for the antigen (if there is antigen available, a very high proportion of it must bind to the antibody). In an immunoassay, both the presence of antigen or antibodies can be measured. For instance, when detecting infection the presence of antibody against the pathogen is measured. For measuring hormones such as insulin, the insulin acts as the antigen.

Conventionally, for numerical results, the response of the fluid being measured must be compared to standards of a known concentration. This is usually done though the plotting of a standard curve on a graph, the position of the curve at response of the unknown is then examined, and so the quantity of the unknown found. The detection of the quantity present of antibody or antigen can be achieved by a variety of methods. One of the most common is to label either the antigen or antibody. The label may consist of an enzyme, radioisotopes, or a fluorophore.

An increasing amount of biological assays, such as immunoassays and gene sequencing, are being carried out on microarrays, such as DNA microarrays or protein microarrays. A microarray is a collection of microscopic spots, such as NDA or protein spots attached to a solid surface, such as glass, plastic or silicon chip forming an array. The microarrays can be used to measure the expression levels of large numbers of genes or proteins simultaneously. The biomolecules, such as DNAs or proteins, on microarray chip typically are detected through optical readout of fluorescent labels attached to a target molecule that is specifically attached or hybridized to a probe molecule. These optical methods are difficult to implement and miniaturize because they rely on the use of optical labels and require large or expensive instrumentation.

A specific type of cell and biomolecule separation and detection method uses microfluidic devices to conduct high throughput separation and analysis based on accurate flow controls through the microfluidic channels. By designing patterned fluidic channels, or channels with specific dimensions in the micro or sub-micro scales, often on a small chip, one is able to carry out multiple assays simultaneously. The cells and biomolecules in microfluidic assays typically are detected through optical readout of fluorescent labels attached to a target cell or molecule that is specifically attached or hybridized to a probe molecule.

BRIEF DESCRIPTION OF THE DRAWINGS

FIG. 1 shows a schematic of a conventional sandwich-type solid-phase immunoassay.

FIG. 2 illustrates a detection method used in a conventional solid-phase immunoassay.

FIG. 3 illustrates typical steps in a conventional sandwich-type solid-phase immunoassay.

FIG. 4 illustrates the disassociation of labels or label-conjugated molecules from the surface of the substrate in an immunoassay.

FIG. 5 illustrates the detection of individual labels in an analyzer.

FIG. 6 illustrates a system wherein an assay unit and a detection unit are contained in a single device.

DETAILED DESCRIPTION

A biological sample often contains many thousands or even more types of biomolecules and clinical diagnosis needs to measure multiple analytes for disease confirmation. Currently, each analyte is measured separately, which requires multiple samples from a patient. The procedure is time consuming and labor intensive. Multiplex assays, in which multiple analytes can be measured at the same time, have been developed to solve this problem. However, in conventional multiplex assays, the detection of different types of labels, such as nanoparticles, are not effective due to signal difference and/or shot noises. For example, when nanoparticles are used as labels, if the nanoparticles of different kinds generate optical signatures over the same spectral range, the shot noise from the superposed signal would limit the detection of nanoparticles of low quantity.

Current methods to solve the problem of signal difference and shot noise described above include subspot scanning, in which small laser spots (typically at diffraction limit) is scanned over a sample. Since the area illuminated by the laser spots are smaller, the number of nanoparticles within the laser spot is reduced. However, for certain samples, reducing the laser spots is not enough to decrease the shot noise from the superposed signal. Furthermore, reducing the laser spots increases the scanning time to cover a certain sample area and, with very small laser spots, the scanning time may be prohibitively long.

The embodiments of the invention allow further particle separation such that the labels can be detected and analyzed in a more accurate and specific manner. In addition, the embodiments of the invention allow the detection of particles individually or single particle detection, thus further enhancing the accuracy of biological assays.

In the embodiments of the invention, analytes that can be detected include antigens of all types, such as proteins, polysaccharides, and small molecules coupled to a protein. The specific bindings between antigens and their corresponding antibodies form the basis of immunoassays. Antibodies suitable for the embodiments of the invention include monoclonal antibodies, polyclonal antibodies, recombinant antibodies, random peptides and aptamers. Immunoassays suitable for the embodiments of the invention include solid-phase immunoassays based the sandwich principle and the competing principle. Also included are specific types of immunoassays such as enzyme-linked immunosorbent assay (ELISA) and electrochemiluminescence (ECL).

Analytes in the embodiments of the invention also include nucleic acids (DNA and RNA), which can form double-stranded molecules by hybridization, that is, complementary base pairing. The specificity of nucleic acid hybridization is such that the detection of molecular and/or nanomaterials binding events can be done through electrical readout of polarization changes caused by the interaction of charged target molecules (DNA, RNA, proteins, for example) and chemically modified nanomaterials (carbon nanotubes, nanowires, nanoparticles functionalized with DNA, for example) with complementary molecular probes (DNA, RNA, anti-body, for example) attached to the electrodes (such as Au, Pt, for example). This specificity of complementary base pairing also allows thousands of hybridization to be carried out simultaneously in the same experiment on a DNA chip (also called a DNA array).

Molecular probes or capture molecules are immobilized on the surface of individually addressable electrode arrays through the surface functionalization techniques. Electrodes allow polarization changes to be electrically detected. The polymer arrays of the embodiment of the invention could be a DNA array (collections of DNA probes on a shared base) comprising a dense grid of spots (often called elements or pads) arranged on a miniature support. Each spot could represent a different gene.

The capture molecule or probe in a DNA chip is usually hybridized with a complex RNA or cDNA target generated by making DNA copies of a complex mixture of RNA molecules derived from a particular cell type (source). The composition of such a target reflects the level of individual RNA molecules in the source. The intensities of the signals resulting from the binding events from the DNA spots of the DNA chip after hybridization between the probe and the target represent the relative expression levels of the genes of the source.

The DNA chip could be used for differential gene expression between samples (e.g., healthy tissue versus diseased tissue) to search for various specific genes (e.g., connected with an infectious agent) or in gene polymorphism and expression analysis. Particularly, the DNA chip could be used to investigate expression of various genes connected with various diseases in order to find causes of these diseases and to enable accurate treatments.

Using embodiments of the invention, one could find a specific segment of a nucleic acid of a gene, i.e., find a site with a particular order of bases in the examined gene. This detection could be performed by using a diagnostic polynucleotide made up of short synthetically assembled single-chained complementary polynucleotide—a chain of bases organized in a mirror order to which the specific segment of the nucleic acid would attach (hybridize) via A-T or G-C bonds.

The practice of the embodiments of the invention may employ, unless otherwise indicated, conventional techniques of organic chemistry, polymer technology, molecular biology (including recombinant techniques), cell biology, biochemistry, and immunology, which are within the skill of the art. Such conventional techniques include polymer array synthesis, immunoassays, hybridization, ligation, detection of molecules, such as antibodies and hybridization using a label. Specific illustrations of suitable techniques can be had by reference to the example herein below. However, other equivalent conventional procedures can, of course, also be used.

As used in the specification and claims, the singular forms "a", "an" and "the" include plural references unless the context clearly dictates otherwise. For example, the term "an array" may include a plurality of arrays unless the context clearly dictates otherwise.

An "array," "macroarray" or "microarray" is an intentionally created collection of molecules which can be prepared either synthetically or biosynthetically. The molecules in the array can be identical or different from each other. The array can assume a variety of formats, e.g., libraries of soluble molecules; libraries of compounds tethered to resin beads, silica chips, or other solid supports. The array could either be a macroarray or a microarray, depending on the size of the pads on the array. A macroarray generally contains pad sizes of about 300 microns or larger and can be easily imaged by gel and blot scanners. A microarray would generally contain pad sizes of less than 300 microns.

"Solid support," "support," and "substrate" refer to a material or group of materials having a rigid or semi-rigid surface or surfaces. In some aspects, at least one surface of the solid support will be substantially flat, although in some aspects it may be desirable to physically separate synthesis regions for different molecules with, for example, wells, raised regions, pins, etched trenches, or the like. In certain aspects, the solid support(s) will take the form of beads, resins, gels, microspheres, or other geometric configurations.

The term "analyte," "target" or "target molecule" refers to a molecule of interest that is to be detected and/or analyzed, e.g., a nucleotide, an oligonucleotide, a polynucleotide, a peptide, or a protein. The analyte, target or target molecule could be a small molecule, biomolecule, or nanomaterial such as but not necessarily limited to a small molecule that is biologically active, nucleic acids and their sequences, peptides and polypeptides, as well as nanostructure materials chemically modified with biomolecules or small molecules capable of binding to molecular probes such as chemically modified carbon nanotubes, carbon nanotube bundles, nanowires, nanoclusters or nanoparticles. The target molecule may be a fluorescently labeled antigen, antibody, DNA or RNA.

The term "capture molecule" refers to a molecule that is immobilized on a surface. The capture molecule is generally, but not necessarily, binds to a target or target molecule. The capture molecule is typically an antibody, a nucleotide, an oligonucleotide, a polynucleotide, a peptide, or a protein, but could also be a small molecule, biomolecule, or nanomaterial such as but not necessarily limited to a small molecule that is biologically active, nucleic acids and their sequences, peptides and polypeptides, as well as nanostructure materials chemically modified with biomolecules or small molecules capable of binding to a target molecule that is bound to a probe molecule to form a complex of the capture molecule, target molecule and the probe molecule. In the case of a solid-phase immunoassay, the capture molecule in immobilized on the surface of the substrate and is an antibody specific to the target, an antigen, to be detected. The capture molecule may be fluorescently labeled antibody, protein, DNA or RNA. The capture molecule may or may not be capable of binding to just the target molecule or just the probe molecule.

The term "probe" or "probe molecule" refers to a molecule that binds to a target molecule for the analysis of the target. The probe or probe molecule is generally, but not necessarily, has a known molecular structure or sequence. The probe or probe molecule may or may not be attached to the substrate of the array. The probe or probe molecule is typically an antibody, a nucleotide, an oligonucleotide, a polynucleotide, a peptide, or a protein, including, for example, monoclonal antibody, cDNA or pre-synthesized polynucleotide deposited on the array. Probes molecules are biomolecules capable of undergoing binding or molecular recognition events with target molecules. (In some references, the terms "target" and "probe" are defined opposite to the definitions provided here.) In immunoassays, the probe molecule may be a labeled antibody specific to the target, an antigen, to be analyzed. In such case, the capture molecule, the target molecule and the probe molecule form a "sandwich." The polynucleotide probes require only the sequence information of genes, and thereby can exploit the genome sequences of an organism. In cDNA arrays, there could be cross-hybridization due to sequence homologies among members of a gene family. Polynucleotide arrays can be specifically designed to differentiate between highly homologous members of a gene family as well as spliced forms of the same gene (exon-specific). Polynucleotide arrays of the embodiment of this invention could also be designed to allow detection of mutations and single nucleotide polymorphism. A probe or probe molecule can be a capture molecule.

A "binding partner," refers to a molecule or aggregate that has binding affinity for one or more analytes, targets or other molecules. In this sense, a binding partner is either a "capture molecule" or a "probe molecule." Within the scope of the embodiments of the invention, virtually any molecule or aggregate that has a binding affinity for an analyte or target of interest may be a binding partner, including, but are not limited to, polyclonal antibodies, monoclonal antibodies, single-chain antibodies, chimeric antibodies, humanized antibodies, antibody fragments, oligonucleotides, polynucleotides, nucleic acids, aptamers, nucleic acid ligands and any other known ligand that can bind to at least one target molecule. Although, in certain embodiments a binding partner is specific for binding to a single target, in other embodiments the binding partner may bind to multiple targets that possess similar structures or binding domains.

"Binding" refers to an interaction between two or more substances, such as between a target and a capture or probe molecule, that results in a sufficiently stable complex so as to permit detection of the bound molecule complex. In certain embodiments of the invention, binding may also refer to an interaction between a second molecule and a target.

"Associated with" or "association" refers to a direct or indirect interactions between two or more substances, such as between a target and a capture or probe molecule, that results in a sufficiently stable complex. For example, a molecule or complex of molecules is "associated with" the surface of a substrate when the molecule or complex is either bound to the surface of the substrate directly, through another molecule or substance, or to both. In other words, substances are "associated with" each other when any one member of the substances is directly bound to at least another member of the substances.

The terms "label" and "tag" are used interchangeably to refer to a marker or indicator distinguishable by the observer but not necessarily by the system used to identify an analyte or target. Labels are often used in biological assays to be conjugated with, or attached to, an otherwise difficult to detect substance. At the same time, Labels usually do not change or affect the underlining assay process. A label or tag used in biological assays include, but not limited to, a radioactive material, a magnetic material, quantum dot, an enzyme, a liposome-based label, a chromophore, a fluorophore, a dye, a nanoparticle, a composite-organic-inorganic nano-cluster, a colloidal metal particle, or a combination thereof.

The terms "die," "polymer array chip," "array," "array chip," or "bio-chip" are used interchangeably and refer to a collection of a large number of capture molecules arranged on a shared substrate which could be a portion of a silicon wafer, a nylon strip or a glass slide. The term "DNA array" or "DNA array chip" is used when the array chip is used to analyze a nucleotide. The term "protein array" is used when the array chip is used to analyze a protein.

The term "chip" or "microchip" refers to a microelectronic device made of semiconductor material and having one or more integrated circuits or one or more devices. A "chip" or "microchip" is typically a section of a wafer and made by slicing the wafer. A "chip" or "microchip" may comprise many miniature transistors and other electronic components on a single thin rectangle of silicon, sapphire, germanium, silicon nitride, silicon germanium, or of any other semiconductor material. A microchip can contain dozens, hundreds, or millions of electronic components.

The term "molecule" generally refers to a macromolecule or polymer as described herein. However, arrays comprising single molecules, as opposed to macromolecules or polymers, are also within the scope of the embodiments of the invention.

The terms "probe volume" and "detection volume" are used interchangeably and refer to a region or space within which a valid measurement of a substance within the region can be obtained. Many factors affect the probe volume and it may be difficult to obtain in certain situations. For example the dimension of a probe volume may be affected by the detection instrument used, the dimension and geography of the substance defining the probe volume region, such as a microfluidic channel, and the fluid dynamic characters of fluid containing the to be measured substances. In some situations, the probe volume dimension may best be measured in situ. For example, when measuring specific substances, such as a fluorescently or otherwise tagged antibody or DNA fragment, contained in a liquid flowing through a microfluidic channel, the probe volume may be best determined in situ, according to specific factors such as the detector used, the dimension of the microfluidic channel, and the fluid dynamic characters of the liquid containing the substances.

"Micro-Electro-Mechanical System (MEMS)" is the integration of mechanical elements, sensors, actuators, and electronics on a common silicon substrate through microfabrication technology. While the electronics are fabricated using integrated circuit (IC) process sequences (e.g., CMOS, Bipolar, or BICMOS processes), the micromechanical components could be fabricated using compatible "micromachining" processes that selectively etch away parts of the silicon wafer or add new structural layers to form the mechanical and electromechanical devices. Microelectronic integrated circuits can be thought of as the "brains" of a system and MEMS augments this decision-making capability with "eyes" and "arms", to allow Microsystems to sense and control the environment. Sensors gather information from the environment through measuring mechanical, thermal, biological, chemical, optical, and magnetic phenomena. The electronics then process the information derived from the sensors and through some decision making capability direct the actuators to respond by moving, positioning, regulating, pumping, and filtering, thereby controlling the environment for some desired outcome or purpose. Because MEMS devices are manufactured using batch fabrication techniques similar to those used for integrated circuits, unprecedented levels of functionality, reliability, and sophistication can be placed on a small silicon chip at a relatively low cost.

"Microprocessor" is a processor on an integrated circuit (IC) chip. The processor may be one or more processor on one or more IC chip. The chip is typically a silicon chip with thousands of electronic components that serves as a central processing unit (CPU) of a computer or a computing device.

A "macromolecule" or "polymer" comprises two or more monomers covalently joined. The monomers may be joined one at a time or in strings of multiple monomers, ordinarily known as "oligomers." Thus, for example, one monomer and a string of five monomers may be joined to form a macromolecule or polymer of six monomers. Similarly, a string of fifty monomers may be joined with a string of hundred monomers to form a macromolecule or polymer of one hundred and fifty monomers. The term polymer as used herein includes, for example, both linear and cyclic polymers of nucleic acids, polynucleotides, polynucleotides, polysaccharides, oligosaccharides, proteins, polypeptides, peptides, phospholipids and peptide nucleic acids (PNAs). The peptides include those peptides having either α-, β-, or ω-amino acids. In addition, polymers include heteropolymers in which a known drug is covalently bound to any of the above, polyurethanes, polyesters, polycarbonates, polyureas, polyamides, polyethyleneimines, polyarylene sulfides, polysiloxanes, polyimides, polyacetates, or other polymers which will be apparent upon review of this disclosure.

A "nanomaterial" as used herein refers to a structure, a device or a system having a dimension at the atomic, molecular or macromolecular levels, in the length scale of approximately 1-100 nanometer range. Preferably, a nanomaterial has properties and functions because of the size and can be manipulated and controlled on the atomic level.

The term "biomolecule" refers to any organic molecule that is part of a living organism. Biomolecules includes a nucleotide, a polynucleotide, an oligonucleotide, a peptide, a protein, a ligand, a receptor, among others. A "complex of a biomolecule" refers to a structure made up of two or more types of biomolecules. Examples of a complex of biomolecule include a cell or viral particles. A cell can include bacteria, fungi, animal mammalian cell, for example.

The term "nucleotide" includes deoxynucleotides and analogs thereof. These analogs are those molecules having some structural features in common with a naturally occurring nucleotide such that when incorporated into a polynucleotide sequence, they allow hybridization with a complementary polynucleotide in solution. Typically, these analogs are derived from naturally occurring nucleotides by replacing and/or modifying the base, the ribose or the phosphodiester moiety. The changes can be tailor-made to stabilize or destabilize hybrid formation, or to enhance the specificity of hybridization with a complementary polynucleotide sequence as desired, or to enhance stability of the polynucleotide.

The term "polynucleotide" or "nucleic acid" as used herein refers to a polymeric form of nucleotides of any length, either ribonucleotides or deoxyribonucleotides, that comprise purine and pyrimidine bases, or other natural, chemically or biochemically modified, non-natural, or derivatized nucleotide bases. Polynucleotides of the embodiments of the invention include sequences of deoxyribopolynucleotide (DNA), ribopolynucleotide (RNA), or DNA copies of ribopolynucleotide (cDNA) which may be isolated from natural sources, recombinantly produced, or artificially synthesized. A further example of a polynucleotide of the embodiments of the invention may be polyamide polynucleotide (PNA). The polynucleotides and nucleic acids may exist as single-stranded or double-stranded. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. The polymers made of nucleotides such as nucleic acids, polynucleotides and polynucleotides may also be referred to herein as "nucleotide polymers."

An "oligonucleotide" is a polynucleotide having 2 to 20 nucleotides. Analogs also include protected and/or modified monomers as are conventionally used in polynucleotide synthesis. As one of skill in the art is well aware, polynucleotide synthesis uses a variety of base-protected nucleoside derivatives in which one or more of the nitrogen atoms of the purine and pyrimidine moiety are protected by groups such as dimethoxytrityl, benzyl, tert-butyl, isobutyl and the like.

For instance, structural groups are optionally added to the ribose or base of a nucleoside for incorporation into a polynucleotide, such as a methyl, propyl or allyl group at the 2'-O position on the ribose, or a fluoro group which substitutes for the 2'-O group, or a bromo group on the ribonucleoside base. 2'-O-methyloligoribonucleotides (2'-O-MeORNs) have a higher affinity for complementary polynucleotides (especially RNA) than their unmodified counterparts. Alternatively, deazapurines and deazapyrimidines in which one or more N atoms of the purine or pyrimidine heterocyclic ring are replaced by C atoms can also be used.

The phosphodiester linkage or "sugar-phosphate backbone" of the polynucleotide can also be substituted or modified, for instance with methyl phosphonates, O-methyl phosphates or phosphororthioates. Another example of a polynucleotide comprising such modified linkages for purposes of this disclosure includes "peptide polynucleotides" in which a polyamide backbone is attached to polynucleotide bases, or modified polynucleotide bases. Peptide polynucleotides which comprise a polyamide backbone and the bases found in naturally occurring nucleotides are commercially available.

Nucleotides with modified bases can also be used in the embodiments of the invention. Some examples of base modifications include 2-aminoadenine, 5-methylcytosine, 5-(propyn-1-yl)cytosine, 5-(propyn-1-yl)uracil, 5-bromouracil, 5-bromocytosine, hydroxymethylcytosine, methyluracil, hydroxymethyluracil, and dihydroxypentyluracil which can be incorporated into polynucleotides in order to modify binding affinity for complementary polynucleotides.

Groups can also be linked to various positions on the nucleoside sugar ring or on the purine or pyrimidine rings which may stabilize the duplex by electrostatic interactions with the negatively charged phosphate backbone, or through interactions in the major and minor groves. For example, adenosine and guanosine nucleotides can be substituted at the $N^2$ position with an imidazolyl propyl group, increasing duplex stability. Universal base analogues such as 3-nitropyrrole and 5-nitroindole can also be included. A variety of modified polynucleotides suitable for use in the embodiments of the invention are described in the literature.

When the macromolecule of interest is a peptide, the amino acids can be any amino acids, including α, β, or ω-amino acids. When the amino acids are α-amino acids, either the L-optical isomer or the D-optical isomer may be used. Additionally, unnatural amino acids, for example, β-alanine, phenylglycine and homoarginine are also contemplated by the embodiments of the invention. These amino acids are well-known in the art.

A "peptide" is a polymer in which the monomers are amino acids and which are joined together through amide bonds and alternatively referred to as a polypeptide. In the context of this specification it should be appreciated that the amino acids may be the L-optical isomer or the D-optical isomer. Peptides are two or more amino acid monomers long, and often more than 20 amino acid monomers long.

A "protein" is a long polymer of amino acids linked via peptide bonds and which may be composed of two or more polypeptide chains. More specifically, the term "protein" refers to a molecule composed of one or more chains of amino acids in a specific order; for example, the order as determined by the base sequence of nucleotides in the gene coding for the protein. Proteins are essential for the structure, function, and regulation of the body's cells, tissues, and organs, and each protein has unique functions. Examples are hormones, enzymes, and antibodies.

The term "sequence" refers to the particular ordering of monomers within a macromolecule and it may be referred to herein as the sequence of the macromolecule.

The term "hybridization" refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." For example, hybridization refers to the formation of hybrids between a probe polynucleotide (e.g., a polynucleotide of the invention which may include substitutions, deletion, and/or additions) and a specific target polynucleotide (e.g., an analyte polynucleotide) wherein the probe preferentially hybridizes to the specific target polynucleotide and substantially does not hybridize to polynucleotides consisting of sequences which are not substantially complementary to the target polynucleotide. However, it will be recognized by those of skill that the minimum length of a polynucleotide desired for specific hybridization to a target polynucleotide will depend on several factors: G/C content, positioning of mismatched bases (if any), degree of uniqueness of the sequence as compared to the population of target polynucleotides, and chemical nature of the polynucleotide (e.g., methylphosphonate backbone, phosphorothiolate, etc.), among others.

Methods for conducting polynucleotide hybridization assays have been well developed in the art. Hybridization assay procedures and conditions will vary depending on the application and are selected in accordance with the general binding methods known in the art.

It is appreciated that the ability of two single stranded polynucleotides to hybridize will depend upon factors such as their degree of complementarity as well as the stringency of the hybridization reaction conditions.

A "ligand" is a molecule that is recognized by a particular receptor. Examples of ligands that can be investigated by this invention include, but are not restricted to, agonists and antagonists for cell membrane receptors, toxins and venoms, viral epitopes, hormones, hormone receptors, peptides, enzymes, enzyme substrates, cofactors, drugs (e.g. opiates, steroids, etc.), lectins, sugars, polynucleotides, nucleic acids, oligosaccharides, proteins, and monoclonal antibodies.

A "receptor" is molecule that has an affinity for a given ligand. Receptors may-be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term "receptors" is used herein, no difference in meaning is intended. A "Ligand Receptor Pair" is formed when two macromolecules have combined through molecular recognition to form a complex. Other examples of receptors which can be investigated by this invention include but are not restricted to:

a) Microorganism receptors: Determination of ligands which bind to receptors, such as specific transport proteins or enzymes essential to survival of microorganisms, is useful in developing a new class of antibiotics. Of particular value would be antibiotics against opportunistic fungi, protozoa, and those bacteria resistant to the antibiotics in current use.

b) Enzymes: For instance, one type of receptor is the binding site of enzymes such as the enzymes responsible for cleaving neurotransmitters; determination of ligands which bind to certain receptors to modulate the action of the enzymes which cleave the different neurotransmitters is useful in the development of drugs which can be used in the treatment of disorders of neurotransmission.

c) Antibodies: For instance, the invention may be useful in investigating the ligand-binding site on the antibody molecule which combines with the epitope of an antigen of interest; determining a sequence that mimics an antigenic epitope may lead to the-development of vaccines of which the immunogen is based on one or more of such sequences or lead to the development of related diagnostic agents or compounds useful in therapeutic treatments such as for auto-immune diseases (e.g., by blocking the binding of the "anti-self" antibodies).

d) Nucleic Acids: Sequences of nucleic acids may be synthesized to establish DNA or RNA binding sequences.

e) Catalytic Polypeptides: Polymers, preferably polypeptides, which are capable of promoting a chemical reaction involving the conversion of one or more reactants to one or more products. Such polypeptides generally include a binding site specific for at least one reactant or reaction intermediate and an active functionality proximate to the binding site, which functionality is capable of chemically modifying the bound reactant.

f) Hormone receptors: Examples of hormones receptors include, e.g., the receptors for insulin and growth hormone. Determination of the ligands which bind with high affinity to a receptor is useful in the development of, for example, an oral replacement of the daily injections which diabetics take to relieve the symptoms of diabetes. Other examples are the vasoconstrictive hormone receptors; determination of those ligands which bind to a receptor may lead to the development of drugs to control blood pressure.

g) Opiate receptors: Determination of ligands which bind to the opiate receptors in the brain is useful in the development of less-addictive replacements for morphine and related drugs.

A "fluorophore" or "fluorescent compound" can include, but is not limited to, a dye, intrinsically fluorescent protein, lanthanide phosphor, and the like. Dyes, for example, include rhodamine and derivatives, such as Texas Red, ROX (6-carboxy-X-rhodamine), rhodamine-NHS, and TAMRA (5/6-carboxytetramethyl rhodamine NHS); fluorescein and derivatives, such as 5-bromomethyl fluorescein and FAM (5'-carboxyfluorescein NHS), Lucifer Yellow, IAEDANS, 7-Me$_2$, N-coumarin-4-acetate, 7-OH-4-CH$_3$-coumarin-3-acetate, 7-NH$_2$-4CH$_3$-coumarin-3-acetate (AMCA), monobromobimane, pyrene trisulfonates, such as Cascade Blue, and monobromotrimethyl-ammoniobimane.

The term "complementary" refers to the topological compatibility or matching together of interacting surfaces of a ligand molecule and its receptor. Thus, the receptor and its ligand can be described as complementary, and furthermore, the contact surface characteristics are complementary to each other.

The terms "spectrum" or "spectra" refer to the intensities of electromagnetic radiation as a function of wavelength or other equivalent units, such as wavenumber, frequency, and energy level.

The term "spectrometer" refers to an instrument equipped with scales for measuring wavelengths or intensities of electromagnetic radiations at a certain wavelength or wavelengths.

One embodiment of the present invention relates to a method of performing a biological assay and detecting biomolecules or small particles. The method comprises: (1) providing a substrate and a complex associated with a surface of the substrate, wherein the complex comprises a first binding partner immobilized on a surface of the substrate, an analyte bound to the first binding partner, a second binding partner bound to the analyte and a label bound to the second binding partner; (2) disassociating the label with the surface of the substrate; and (3) detecting the disassociated label.

In the embodiment of the invention, the substrate comprises a polymer, silicon or glass. Specific materials useful as the substrate include, but not limited to, polystyrene, polydimethylsiloxane (PDMS), silicon, glass, chemically functionalized glass, polymer-coated glass, nitrocellulose coated glass, uncoated glass, quartz, natural hydrogel, synthetic hydrogel, plastics, metals, and ceramics. The substrate may comprise any platform or device currently used for carrying out immunoassays, DNA or protein microarray analysis. Thus, the substrate may comprise a microarray or a macroarray, a multi-well plate, a microfluidic device, an integrated circuit, MEMS, or a combination thereof. Furthermore, the substrate may not be flat, and may comprise beads, particles, or other shaped objects.

In the embodiments of the invention, the first binding partner is immobilized on a surface of the substrate. The immobilization may be permanent or reversible. The immobilization can be by forming a covalent bond between the first binding partner and the surface or any functional group on the surface, or by other chemical/physical mechanisms. The binding of the first binding partner to the surface facilitates the association of the complex with the surface. As discussed herein, the complex is "associated with" the surface of the substrate when any member of the complex is bound to the surface of the substrate directly. In the embodiment of the invention, the complex comprises a first binding partner that is immobilized on the surface of the substrate, an analyte that is bound to the first binding partner, a second binding partner that is bound to the analyte and a label that is bound to the second binding partner. Under this circumstance, the label, the second binding partner and the analytes are also "associated with" the surface of the substrate. In the embodiment, the analyte, the second binding partner and the label may or may not be bound to the surface of the substrate directly. Further, the label may or may not be bound to the analyte directly.

In the embodiments of the invention, the analyte encompasses any compound, molecule or aggregate of interest for detection or analysis. Non-limiting examples of the analyte include an antibody, protein, peptide, receptor, antigen, allergen, carbohydrate, polysaccharide, glycoprotein, growth factor, cytokine, lipid, hormone, metabolite, cofactor, inhibitor, drug, pharmaceutical, poison, explosive, pesticide, nutrient, toxin, chemical warfare agent, biowarfare agent, biohazardous agent, infectious agent, prion, radioisotope, vitamin, carcinogen, mutagen, narcotic, heterocyclic aromatic compound, amphetamine, barbiturate, hallucinogen, waste product, and contaminant.

In one embodiment of the invention, the analyte comprises a biomolecule. More specifically, the analyte comprises an antigen, antibody, protein, virus, DNA, RNA, polynucleotide, nucleic acid, a carbohydrate, lipid, a bacterium, or a macromolecule.

In the embodiments of the invention, the first binding partner or the second binding partner comprises, independently an antibody, such as a polyclonal antibody, monoclonal antibody, single-chain antibody, chimeric antibody, humanized antibody, antibody fragments, an antigen, a oligonucleotide, a polynucleotide, a nucleic acids, an aptamer, a nucleic acid ligand and any other known ligand that can bind to at least one target molecule In one embodiment of the invention, the analyte comprises an antigen and the first and second binding partners independently comprise an antibody to the antigen. The embodiment encompasses part of all of a sandwich type immunoassay, such as an ELISA type of detection assay, in which the first binding partner, or the capture molecule, is an antibody with affinity for the analyte, usually an antigen. After binding of the analyte to first binding partner, a second molecule, the second binding partner or probe molecule, which is typically a tagged antibody with an affinity for a different epitope of the analyte, is added and the complex of first binding partner/analyte/second binding partner with label is detected. In alternative embodiments, the first binding partner may have affinity for an analyte while the second binding partner has affinity for the first binding partner. Although detection may involve the use of a tagged second binding partner with affinity for the analyte, in alternative embodiments the first binding partner or the analyte may also be tagged for detection. The skilled artisan will be familiar with a variety of techniques by which an analyte/binding partner complex may be detected, any of which may be utilized within the scope of the embodiments of the invention.

In another embodiment of the invention, the analyte comprises a polynucleotide, such as a DNA or RNA, and the first and second binding partners independently comprise a complementary polynucleotide. The embodiment encompasses part of all of a sandwich type hybridization assay, in which the first binding partner, or the capture molecule/sequence, is a polynucleotide complementary to the analyte polynucleotide, usually a DNA sequence. After binding of the analyte to the first binding partner, a second molecule, the second binding partner or probe molecule/sequence, which is typically a tagged DNA sequence, is added and the complex of first binding partner/analyte/second binding partner with label is detected. In alternative embodiments, the first binding partner may have affinity for an analyte while the second binding partner has affinity for the first binding partner. Although detection may involve the use of a tagged second binding partner with affinity for the analyte, in alternative embodiments the first binding partner or the analyte may also be tagged for detection. The skilled artisan will be familiar with a variety of techniques by which an analyte/binding partner complex may be detected, any of which may be utilized within the scope of the embodiments of the invention.

In the embodiment of the invention, the label comprises a detectable label or tag attached to, or conjugated with the second binding partner, the analyte or the first binding partner. In a specific embodiment, the label is attached to, or conjugated with the second binding partner. In the embodiments of the invention, the label comprises a radio-active material, a magnetic material, quantum dot, an enzyme, a liposome-based label, a chromophore, a fluorophore, a dye, a nanoparticle, a composite-organic-inorganic nano-cluster, a colloidal metal particle, or a combination thereof.

In the embodiments of the invention, the label is detectable by means of a fluorescence detector, a spectrophotometer, a Raman spectrophotometer, a magnetic detector, a magnetic tunnel junction sensor, a proximity scintillation surface, a luminometer, a scintillation counter, a charge coupled device camera or a gamma counter.

In one embodiment of the invention, the association of the complex with the surface of the substrate comprises: (1) immobilizing the first binding partner on the surface of the substrate; (2) binding the analyte with the first binding partner; and (3) binding a label-conjugated second binding partner with the analyte. The embodiment of the invention encompasses a sandwich type immunoassay or DNA microarray assay. In such assays, a first binding partner, such as an antibody or capture DNA molecule is first immobilized on the surface of the substrate, e.g., a glass slide or microarray. The analyte, such as an antigen or target DNA molecule, is then bound to the first binding partner. A second binding partner, such as an antibody or probe DNA molecule, conjugated with, or attached to a label, such a tag or label, is bound to the analyte. The complex of analyte/second binding partner/label is now associated with the surface of the substrate. In the embodiment of the invention, the analyte may or may not be bound to the surface of the substrate. The second binding partner may or may not be bound to the surface of the substrate or the first binding partner and that the label may or may be bound to the analyte, the first binding partner or the surface of the substrate.

In one embodiment of the invention, the immobilization of the first binding partner to the surface of the substrate comprises contacting the surface of the substrate with a buffer comprising the first binding partner, incubating the buffer, and washing the surface. Any suitable buffer may be used for the immobilization. The temperature and duration of the incubation process will be determined according to the substrate, the first binding partner, and the subsequent binding events. Also, the first binding partner may be immobilized in a predetermined pattern to form a desired array. The washing step helps to remove any non-binding substance and prepare the surface for the subsequent procedures.

In a specific embodiment, after the immobilization of the first binding partner, a buffer containing a blocking agent is applied over the surface of the substrate. The buffer is then incubated and the surface is washed. The blocking agent helps to block non-specific binding spots on the surface of the substrate, such that the specific binding abilities of the first binding partner are expressed more prominently. Any suitable blocking agent, such as albumin, may be used for the embodiment.

In another embodiment of the invention, the binding of the analyte with the first binding partner comprises contacting the surface of the substrate with a buffer comprising the analyte, incubating the buffer, and washing the surface. In the embodiment, any suitable buffer may be used for the binding event. The temperature and duration of the incubation process will be determined according to the analyte and the first binding partner used and the subsequent binding events. A skilled artisan would know how to achieve the desired binding effect according to the materials used under the specific situation. The washing step helps to remove any non-binding substance and prepare the surface for the subsequent procedures.

In another embodiment of the invention, the binding of the label-conjugated second binding partner with the analyte comprises contacting the surface of the substrate with a buffer comprising the label-conjugated second binding partner, incubating the buffer, and washing the surface. In the embodiment, the second binding partner is pre-conjugated with a suitable label. Again, any suitable buffer may be used for the binding event. The temperature and duration of the incubation process will be determined according to the analyte, the binding partner and label used and the subsequent binding events. A skilled artisan would know how to achieve the desired binding effect according to the materials used under the specific situation. The washing step helps to remove any non-binding substance and prepare the surface for the subsequent procedures.

In the embodiments of the invention, once the first binding partner is immobilized on the surface of the substrate and the complex of analyte/second binding partner/label is associated with the surface of the substrate, the label is disassociated, or detached or removed, from the surface. As discussed herein, in conventional assays, such as solid-phase immunoassay and DNA microarray assays, the detection is performed when the binding events are complete and the label or tag is still bound to, or associated with the surface of the substrate. Difficulties with the conventional detection methods arise when more than one label/tag is used and there is substantial difference of signal intensities among the different labels. This would lead to very strong signals from labels with strong signal intensities and weak signals from labels with weak signal intensities. Similar problem would also arise when the numbers of one type of labels are drastically different from the numbers of another type of labels. Additional problem would arise when the sample, e.g., the analyte and the first and second binding partner, and the substrate generate strong background signals.

FIGS. 1 and 2 illustrate a conventional sandwich type multiplex immunoassay. As shown in FIG. 1, capture antibodies are immobilized on the surface of a substrate. Target molecules are bound to the corresponding antibodies. Detection antibodies conjugated with labels are then bound to the target molecules. After the completion of the bindings, the labels are illuminated by an excitation beam, e.g., laser, and the optical signals from the labels are detected. FIG. 2 illustrates a representative area on the surface of the substrate wherein different brightness of the labels is detected. As discussed herein, Difficulties with the conventional detection method for multiplex assays arise when there is substantial difference of signal intensities among the different labels, when the numbers of one type of labels are drastically different from the numbers of another type of labels, or when the target molecule, the antibodies, and the substrate generate strong background signals.

The embodiments of the present invention provide methods, systems and devices that help to ameliorate or resolve the above problems. In the embodiments of the invention, the label is disassociated from the surface of the substrate before detection take place. FIGS. 3 and 4 illustrate a comparison between a conventional sandwich type immunoassay and an embodiment of the invention, respectively. As illustrated in FIG. 3, conventional sandwich type immunoassay includes immobilizing a capture antibody on the surface of a substrate, binding the target molecules by the capture molecules, binding label-conjugated antibodies with the target molecules, and detecting the bound complex, as shown in FIGS. 1 & 2.

In comparison, FIG. 4 illustrates an embodiment of the invention. As illustrated, the multiplex immunoassay comprises immobilizing capture antibodies, or first binding partners, on the surface of a substrate, binding the target molecules, or analytes, by the capture molecules, binding label-conjugated antibodies, or second binding partners, with the target molecules, disassociating one or more of the labels, the second binding partners, the analytes, and the first binding partners from one another, and detecting the disassociated labels (not shown). Thus, according to this embodiment of the invention, the detection of the labels is not performed while the labels are still bound to the surface of the substrate. Rather, the detection takes place after the labels, or labels-conjugated molecules, have been disassociated from the surface of the substrate. The disassociation enables different and/or more effective detection of the labels, as discussed herein.

According to the embodiments, the disassociation of the label from the surface of the substrate may be achieved by a number of procedures, including detaching the label from the second binding partner; detaching the second binding partner from the analyte and detaching the analyte from the first binding partner, detaching the first binding partner from the substrate, and detaching part of the substrate from the rest of the substrate.

According to other embodiments of the invention, the disassociating of the label from the surface of the substrate is by means of changing the condition of a buffer within which the complex and the surface of the substrate are immersed, or changing the temperature surrounding the complex and the surface of the substrate. In another embodiment of the invention, the disassociation of the label from the surface of the substrate is by means of introducing a denaturing or digestion agent into a buffer within which the complex and the surface of the substrate are immersed. In another embodiment of the invention, the disassociation may be performed by applying forces (e.g. magnetic, electric, optical), or by applying energies (e.g. microwave, light). MEMS technology may also be used in the disassociation. As disclosed herein, MEMS augments the decision-making capability of microelectronic integrated circuits with "eyes" and "arms" to allow microsystems to sense and control the environment. Sensors gather information from the environment through measuring mechanical, thermal, biological, chemical, optical, and magnetic phenomena, thus allowing or helping the disassociation of the complex from the substrate or even part of the substrate from the rest of the substrate.

According to the embodiments of the invention, disassociation may happen by releasing the label from the second binding partner, the second binding partner from the analyte, the analyte from the first binding partner, and/or the first binding partner from the substrate. The disassociation may be also by way of detaching part of the substrate from the rest of the substrate. In such cases, the part of the substrate being detached may be a part onto which the first binding partner, the analyte, the second binding partner, and/or the label is attached. The disassociation of the part of the substrate may be by force and/or energy. For example, when the part of the substrate comprises a particle, e.g., a magnetic or electrically charged particle, a magnetic and/or electric field may be applied to detach the particle from the rest of the substrate.

In one embodiment of the invention, the disassociated label, label/second binding partner or label/second binding partner/analyte, is collected in a liquid, such as in a suitable buffer, in a container, a reservoir, or a fluidic channel. Collection of the disassociated label helps to prepare the subsequent detection and/or analysis of the label. In one embodiment of the invention, the concentration of the label in the liquid may be changed, such as concentrated or diluted, such that the label concentration is more suitable for the subsequent detection and/or analysis.

In another embodiment of the invention, the liquid containing the disassociated label is flown through one or more microfluidic channel, which may be part of a detection/analysis device. The liquid may be flown through the microfluidic channels in a controlled and predetermined manner such that appropriate detection of the label can be carried out. In the embodiment, any suitable microfluidic detection methods may be used to detect and/or quantify the number of labels contained in the liquid.

In a specific embodiment of the invention, the detecting of the label is by means of a fluorescence detector, a spectrophotometer, a Raman spectrophotometer, a magnetic detector, a magnetic tunnel junction sensor, a proximity scintillation surface, a luminometer, a scintillation counter, a charge coupled device camera or a gamma counter. As understood by skilled artisans, the detecting method and device should be suitable for the specific label, or label/tag, used in the assay. A specific character of the embodiments of the invention is that the labels to be detected are removed from the surface of the substrate, such as a glass slide or a DNA microarray, and collected in a liquid. This way, suitable, and more accurate ways of detection may be designed to overcome some of the drawbacks of detecting the labels on a solid surface. One such suitable detection method, as discussed herein, involves flowing the liquid containing the labels in microfluidic channels under controlled conditions such that the labels can be detected individually.

In one embodiment of the invention, the detection of the label comprises determining the amount of labels disassociated with the surface of the substrate. As discussed herein, the embodiments of the invention encompass situations wherein a plurality of complexes are associated with the surface of the substrate and at least two of the complexes comprise different analytes. The situations are often referred to as multiplex assays, where more than one analytes are to be detected in a single assay. As the different analytes would be labeled with different labels, the detection would involve detecting different labels. In one embodiment of the invention, the detection of the labels comprises determining the amount of each different analytes. Specific situations encompassed by the embodiments of the invention include multiplex immunoassays and DNA microarray assays.

Another embodiment of the invention relates a system for performing biological assays. The system comprises: (1) a substrate; (2) a complex associated with a surface of the substrate, wherein the complex comprises a first binding partner immobilized on a surface of the substrate, an analyte bound to the first binding partner, a second binding partner bound to the analyte and a label bound to the second binding partner; and (3) a detection device capable of detecting the label after the label is disassociated with the surface of the substrate.

In the embodiment of the invention, the substrate comprises a polymer, silicon or glass. Specific materials useful as the substrate include, but not limited to, polystyrene, polydimethylsiloxane (PDMS), silicon, glass, chemically functionalized glass, polymer-coated glass, nitrocellulose coated glass, uncoated glass, quartz, natural hydrogel, synthetic hydrogel, plastics, metals, and ceramics. The substrate may comprise any platform or device currently used for carrying out immunoassays, DNA or protein microarray analysis. Thus, the substrate may comprise a microarray or a macroarray, a multi-well plate, a microfluidic device, an integrated circuit, or a combination thereof.

In the embodiment of the invention, the system comprises a platform or device on which a biological assay is being performed. Specifically, the system comprises a device for performing an immunoassay, such as an ELISA assay, wherein a sandwich type binding of antibody/antigen/antibody has been formed. The system also comprises a DNA microarray assay, wherein a sandwich type capture molecule/target DNA/probe molecule binding has been formed. The system further comprises the detection of the label, or the labeled antibody or probe molecule, after the label has been disassociated from the surface of the substrate.

In the embodiments of the invention, the detection device is designed to detect the labels after the labels have been disassociated from the surface. In one embodiment, the detection device comprises a fluorescence detector, a spectrophotometer, a Raman spectrophotometer, a magnetic detector, a magnetic tunnel junction sensor, a proximity scintillation surface, a luminometer, a scintillation counter, a charge coupled device camera or a gamma counter. In the embodiment, the detector may be a separate unit from the substrate. It may also be integrated into the substrate.

In another embodiment of the invention, the system further comprises a container, a reservoir, or a fluidic channel for collecting a liquid comprising the label after the label is disassociated with the surface of the substrate. In the embodiment, the container, reservoir or fluidic channel may be separate units from the substrate or the detector. They may also be integrated into the substrate and/or the detector. The container, reservoir or fluidic channel is useful in facilitating the collection and/or control of the disassociated labels such that appropriate detection of the labels may be carried out.

In one embodiment of the invention, the liquid comprising the labels is flown through a microfluidic channel and the labels are detected within the microfluidic channel. The liquid may be flown through the microfluidic channel in a controlled and predetermined manner such that appropriate detection of the labels can be carried out. In the embodiment, the detection device comprises a single channel detector, specifically, a photodiode, an avalanche photodiode, or a photo-multiplier tube. Further, the detection device may comprise an optical filter.

In another embodiment of the invention, the liquid comprising the labels is flown through a plurality of microfluidic channels and the labels are detected within the microfluidic channels. The liquid may be flown through the microfluidic channels in a controlled and predetermined manner such that appropriate detection of the labels can be carried out. In the embodiment, the detection device comprises an array detector or a single detector with multiple channels. In a specific embodiment, the detector comprises a photodiode array or a charge-coupled device (CCD). Further, the detection device may comprise a diffraction grating.

Another embodiment of the invention relates to an analyzer for performing biological assays. The analyzer comprises a probe volume, a microfluidic channel, and a detection device, wherein the probe volume is within a portion of the microfluidic channel and the probe volume is adapted to contain no more than one label within the probe volume at any moment. In a specific embodiment, the analyzer is configured that a liquid comprising a plurality of labels passes through the microfluidic channel and that the microfluidic channel, detection device and the liquid are controlled such that the microfluidic channel, the detection device and the liquid passing through the microfluidic channel define a probe volume within a portion of the microfluidic channel, and that there is not more than one label within the probe volume at any moment.

An embodiment of the invention is illustrated in FIG. 5, in which a microfluidic channel, a beam emitting laser and a detector, and a liquid comprising labels or label-conjugated molecules form part of an analyzer. As shown, the liquid flow through the microfluidic channel in such a manner that the laser beam and the detector are able to detect and/or analyze the labels on an individual basis. In one embodiment of the invention, the analyzer is designed such that there is not more than one label within the probe volume at any given time (not shown). This may be achieved by controlling factors such as the dimensions of the microfluidic channel, the laser beam, the detector, and the fluid dynamic characters of the liquid, as discussed herein.

In the embodiments of the invention, the analyzer is especially suitable for detecting labels or tags in a biological assay. In one embodiment, the analyzer comprises a plurality of microfluidic channels and the detection device is suited for multi-channel detection. In another embodiment, the probe volumes in different microfluidic channels may be different. As discussed herein, the dimension of the probe volume may be affected by factors such as the detector used, the dimensions of the microfluidic channels, and the fluid dynamic characters of the liquid. In one embodiment, the probe volume is determined in situ according the specific materials and conditions used.

In one embodiment of the invention, the microfluidic channel has a dimension of about 1 µm to about 500 µm. The channel may have uniform or different cross-sections. Further, the cross-section may have different shapes, such as rectangle or other quadrangles, circle or other conics. Skilled artisans understood that, even though the cross-section of a microfluidic channel may not be mathematically defined shape, the dimension of the channel can still be relatively accurately defined and determined.

In the embodiments of the invention, the microfluidic channel or multiple microfluidic channels may be part of an integrated device, such as an integrated circuit, a microfluidic device, or a MEMS. The microfluidic channels or their integrated devices can be made by using techniques known to skilled artisans or methods disclosed herein. For example, the microfluidic channels may be made by soft lithography method with poly-dimethyl siloxane. With these techniques it is possible to generate patterns with critical dimensions as small as 30 nm. These techniques use transparent, elastomeric polydimethylsiloxane (PDMS) "stamps" with patterned relief on the surface to generate features. The stamps can be prepared by casting prepolymers against masters patterned by conventional lithographic techniques, as well as against other masters of interest. Several different techniques are known collectively as soft lithography. They are as described below:

Near-Field Phase Shift Lithography. A transparent PDMS phase mask with relief on its surface is placed in conformal contact with a layer of photoresist. Light passing through the stamp is modulated in the near-field. If the relief on the surface of the stamp shifts the phase of light by an odd multiple of a predetermined number, a node in the intensity is produced. Features with dimensions between 40 and 100 nm are produced in photoresist at each phase edge.

Replica Molding. A PDMS stamp is cast against a conventionally patterned master. Polyurethane is then molded against the secondary PDMS master. In this way, multiple copies can be made without damaging the original master. The technique can replicate features as small as 30 nm.

Micromolding in Capillaries (MIMIC). Continuous channels are formed when a PDMS stamp is brought into conformal contact with a solid substrate. Capillary action fills the channels with a polymer precursor. The polymer is cured and the stamp is removed. MIMIC is able to generate features down to 1 µm in size.

Microtransfer Molding ((TM). A PDMS stamp is filled with a prepolymer or ceramic precursor and placed on a substrate. The material is cured and the stamp is removed. The technique generates features as small as 250 nm and is able to generate multilayer systems.

Solvent-assisted Microcontact Molding (SAMIM). A small amount of solvent is spread on a patterned PDMS stamp and the stamp is placed on a polymer, such as photoresist. The solvent swells the polymer and causes it to expand to fill the surface relief of the stamp. Features as small as 60 nm have been produced.

Microcontact Printing ((CP). An "ink" of alkanethiols is spread on a patterned PDMS stamp. The stamp is then brought into contact with the substrate, which can range from coinage metals to oxide layers. The thiol ink is transferred to the substrate where it forms a self-assembled monolayer that can act as a resist against etching. Features as small as 300 nm have been made in this way.

Techniques used also include micromachining of silicon for microelectricalmechanical systems (MEMS), and embossing of thermoplastic with patterned quartz. Unlike conventional lithography, these techniques are able to generate features on both curved and reflective substrates and rapidly pattern large areas. A variety of materials could be patterned using the above techniques, including metals and polymers. The methods complement and extend existing nanolithographic techniques and provide new routes to high-quality patterns and structures with feature sizes of about 30 nm.

Standard lithography on silicone wafer or silica glass could also be used to fabricate the devices of the embodiments of this invention. Chambers or channels can be made from the devices, fluidic flow can be controlled by pressure gradient, electrical field gradient, gravity, heat gradient etc. The labels or label-conjugated molecules can also be separated by planar device with a single a plurality of chambers, where the surfaces are modified with polymers (polyethylene glycol (PEG)-dramatized compounds) that can minimize non-specific binding.

In one embodiment of the invention, the probe volume of the analyzer is from about 0.1 (fL) to about 100 µL. As discussed herein, the probe volume is affected by a number of factors including the detector used, the dimensions of the microfluidic channels, and the fluid dynamic characters of the liquid. In the embodiment of the invention, the analyzer is designed such that the liquid passes through the microfluidic channel in a controlled manner and that not more than one label is within the probe volume at any given time. Factors such as the concentration of labels in the liquid and beam profile and intensity from the detector, in addition to factors affecting the probe volume, also affect the number and frequency of labels appearing within the probe volume.

In one embodiment of the invention, the detection device comprises a fluorescence detector, a spectrophotometer, a Raman spectrophotometer, a magnetic detector, a magnetic tunnel junction sensor, a proximity scintillation surface, a luminometer, a scintillation counter, a charge coupled device camera or a gamma counter. In a specific embodiment, the detection device comprises a beam emitter, a spectrometer, and a detector. In another embodiment, the beam emitter is to emit a beam comprising laser.

In yet another embodiment of the invention, the analyzer is adapted to pass a liquid comprising a plurality of labels through the microfluidic channel. More specifically, the passing of the liquid through the microfluidic channel is by means of pressure difference, electrophoresis, electroosmosis, or magnetism. As understood by skilled artisan, liquid flow through microfluidic channels can be achieved and controlled by a number of mechanisms. In a specific embodiment, the passing of the liquid through the microfluidic channel is by a pump, such as a syringe pump.

In one embodiment of the invention, the passing of the liquid through the microfluidic channel is at a flow rate of from approximately 0.01 µL to 500 µL. As discussed herein, the flow rate of the liquid is one of the factors affecting the probe volume and the rate of labels passing through the probe volume. In the embodiment, the flow rate is determined according to factors such as the detector used, the microfluidic channel dimensions, the nature of the liquid and the concentration of the labels within the liquid.

In another embodiment of the invention, the analyzer comprises a microprocessor comprising software or a hardware to process signal or data from the detection device. For example, the phase/intensity information as electrical signals generated by the detector may be read to the microprocessor to transform and generate data, such as an intensity/frequency plot of a spectrum.

Another embodiment of the invention relates to a system for performing biological assays. The system comprise: (1) an assay unit comprising a substrate having a first binding partner immobilized on a surface of the substrate and a complex associated with the surface of the substrate, wherein the complex comprises an analyte bound to the first binding partner, a second binding partner bound to the analyte and a label bound to the second binding partner; and (2) a detection unit comprising a microfluidic channel and a detection device, wherein the detection unit is adapted to detect the label after the label is disassociated with the surface of the substrate.

As illustrated in FIG. 6, the assay unit and the detection unit are part of a system, which may be a single device, such as an integrated circuit or a microfluidic device. The system integrates an assay unit with a detection unit so that a disassociated label, or label-conjugated molecule, from the assay is detected and/or analyzed by the detection unit. In one embodiment of the invention, the label is collected in a liquid after being disassociated with the surface of the substrate. In another embodiment, the system further comprises a containing unit, such as a reservoir or a container, for the liquid.

In another embodiment of the invention, the system is designed that the liquid containing the disassociated label is flown through the microfluidic channel for the detection of the label. In a specific embodiment, the microfluidic channel, the detection device and the liquid flowing through the microfluidic channel define a probe volume within a portion of the microfluidic channel, and wherein there is not more than one label within the probe volume at any moment.

This application discloses several numerical range limitations that support any range within the disclosed numerical ranges even though a precise range limitation is not stated verbatim in the specification because the embodiments of the invention could be practiced throughout the disclosed numerical ranges. Further, the entire disclosure of the patents and publications referred in this application, if any, are hereby incorporated herein in entirety by reference.

The invention claimed is:

1. A method of conducting a multiplex immunoassay comprising:
    providing a substrate and forming a plurality of different complexes associated with a surface of the substrate, wherein the plurality of different complexes comprises a plurality of first binding partners immobilized on the surface of the substrate, a plurality of different analytes bound to the plurality of first binding partners, a plurality of second binding partners bound to the plurality of different analytes and a plurality of different labels bound to the plurality of second binding partners, wherein each of the plurality of different complexes comprises at least one binding partner comprising an antibody;
    disassociating the plurality of different labels from the surface of the substrate;
    flowing said plurality of disassociated labels through a detection device, wherein said detection device comprises at least one microfluidic channel having a probe volume adapted to contain no more than one label at any given time,
    and detecting the plurality of labels on an individual basis by said detection device,
    wherein the substrate comprises (a) an integrated circuit, and (b) a multi-well plate or an array, wherein the array comprises a microarray or a macroarray, further wherein the integrated circuit and the multi-well plate are integrally integrated within the substrate, or the integrated circuit and the array are integrally integrated within the substrate.

2. The method of claim 1, wherein the substrate comprises a polymer, silicon or glass.

3. The method of claim 1, wherein the substrate further comprises a microfluidic device.

4. The method of claim 1, wherein the analyte comprises a biomolecule.

5. The method of claim 1, wherein the analyte comprises an antigen, an antibody, a protein, a virus, a bacterium, a carbohydrate, a lipid, a nucleic acid or a macromolecule.

6. The method of claim 1, wherein the first binding partner or the second binding partner is an antibody and the other binding partner comprises an antibody, an antigen, a receptor, or a ligand.

7. The method of claim 1, wherein the analyte comprises an antigen and the first and second binding partners independently comprises an antibody to the antigen.

8. The method of claim 1, wherein the label comprises a radio-active material, a magnetic material, a quantum dot, an enzyme, a liposome-based label, a chromophore, a fluorophore, a dye, a nanoparticle, a composite-organic-inorganic nano-cluster, a colloidal metal, or a combination thereof.

9. The method of claim 1, wherein the label is detectable by means of a fluorescence detector, a spectrophotometer, a Raman spectrophotometer, a magnetic detector, a magnetic tunnel junction sensor, a proximity scintillation surface, a luminometer, a scintillation counter, a charge coupled device camera or a gamma counter.

10. The method of claim 1, wherein the association of the complex with the surface of the substrate comprises: immobilizing the first binding partner on the surface of the substrate; binding the analyte with the first binding partner; and binding a label-conjugated second binding partner with the analyte.

11. The method of claim 10, wherein the immobilizing of the first binding partner comprises contacting the surface of the substrate with a buffer comprising the first binding partner, incubating the buffer, and washing the surface.

12. The method of claim 11, further comprising applying a buffer comprising a blocking agent over the surface of the substrate, incubating the buffer, and washing the surface.

13. The method of claim 10, wherein the binding of the analyte with the first binding partner comprises contacting the surface of the substrate with a buffer comprising the analyte, incubating the buffer, and washing the surface.

14. The method of claim 10, wherein the binding of the label-conjugated second binding partner with the analyte comprises contacting the surface of the substrate with a buffer comprising the label-conjugated second binding partner, incubating the buffer, and washing the surface.

15. The method of claim 1, wherein the disassociating of the label is by means of detaching the label from the second binding partner.

16. The method of claim 1, wherein the disassociating of the label is by means of detaching the second binding partner from the analyte.

17. The method of claim 1, wherein the disassociating of the label is by means of detaching the analyte from the first binding partner.

18. The method of claim 1, wherein the disassociating of the label is by means of detaching the first binding partner from the surface of the substrate.

19. The method of claim 1, where in the disassociating of the label is by means of detaching a part of the substrate from the rest of the substrate.

20. The method of claim 1, wherein the disassociating of the label is by means of changing the condition of a buffer within which the complex and the surface of the substrate are immersed.

21. The method of claim 1, wherein the disassociating of the label is by means of changing the temperature surrounding the complex and the surface of the substrate.

22. The method of claim 1, wherein the disassociating of the label is by means of introducing a denaturing or digestion agent into a buffer within which the complex and the surface of the substrate are immersed.

23. The method of claim 1, further comprising using a liquid to collect the disassociated label in a container, a reservoir, or a fluidic channel.

24. The method of claim 23, further comprising changing the concentration of the label in the liquid.

25. The method of claim 23, further comprising flowing the liquid through a microfluidic channel.

26. The method of claim 1, wherein the detecting of the label is by means of a fluorescence detector, a spectrophotometer, a Raman spectrophotometer, a magnetic detector, a magnetic tunnel junction sensor, a proximity scintillation surface, a luminometer, a scintillation counter, a charge coupled device camera or a gamma counter.

27. The method of claim 1, wherein the detecting of the label comprises determining the amount of labels disassociated with the surface of the substrate.

28. The method of claim 1, wherein the detecting of the label comprises flowing a liquid comprising the label through a microfluidic channel and detecting the label within the microfluidic channel.

29. The method of claim 1, wherein a plurality of complexes are associated with the surface of the substrate and at least two of the complexes comprise a different analyte.

30. The method of claim 29, wherein the detecting comprises determining the amount of each different analyte.

31. The method of claim 29, wherein the substrate comprises a microarray, and wherein the plurality of complexes are associated with the surface of the microarray and at least two of the complexes comprise a different analyte.

32. The method of claim 1, wherein the substrate further comprises a micro-electro-mechanical system (MEMS).

33. The method of claim 1, wherein the disassociating the plurality of different labels from the surface of the substrate comprises disassociating the plurality of different labels from the plurality of different complexes associated with a surface of the substrate.

34. The method of claim 1, wherein the probe volume has a volume from about 0.1 fL to about 100 μl.

\* \* \* \* \*